US012575765B2

(12) United States Patent
Connell et al.

(10) Patent No.: US 12,575,765 B2
(45) Date of Patent: Mar. 17, 2026

(54) DEVICE FOR NON-INVASIVE SUBSTANCE DETECTION

(71) Applicant: APPLIED MONITORING LIMITED, Sedgefield (GB)

(72) Inventors: Robert Connell, Tyne and Wear (GB); Alex Mason, Tyne and Wear (GB)

(73) Assignee: APPLIED MONITORING LIMITED, Sedgefield (GB)

( * ) Notice: Subject to any disclaimer, the term of this patent is extended or adjusted under 35 U.S.C. 154(b) by 563 days.

(21) Appl. No.: 17/928,783

(22) PCT Filed: May 26, 2021

(86) PCT No.: PCT/GB2021/051283
§ 371 (c)(1),
(2) Date: Nov. 30, 2022

(87) PCT Pub. No.: WO2021/245376
PCT Pub. Date: Dec. 9, 2021

(65) Prior Publication Data
US 2023/0210414 A1     Jul. 6, 2023

(30) Foreign Application Priority Data

Jun. 2, 2020    (GB) ..................................... 2008272

(51) Int. Cl.
*A61B 5/145*        (2006.01)
*A61B 5/00*         (2006.01)
*A61B 5/0507*       (2021.01)

(52) U.S. Cl.
CPC ........ *A61B 5/14546* (2013.01); *A61B 5/0507* (2013.01); *A61B 5/7267* (2013.01)

(58) Field of Classification Search
CPC . A61B 5/14546; A61B 5/0507; A61B 5/7267; A61B 5/6824; A61B 5/7246; A61B 5/4845
See application file for complete search history.

(56) References Cited

U.S. PATENT DOCUMENTS 10,258,243 B2 * 4/2019 LeBoeuf ................ G16H 40/63
2013/0225960 A1   8/2013 Porch et al.
(Continued)

FOREIGN PATENT DOCUMENTS

CN         107782747 A     3/2018
CN        2084047585 U     1/2019
(Continued)

OTHER PUBLICATIONS

Parikha Mehrotra et al: "EM-Wave Biosensors: A Review of RF, Microwave, mm-Wave and Optical Sensing", Sensors,vol. 19, No. 5,Feb. 27, 27, 2019, 46 pages.

*Primary Examiner* — Jeffrey G. Hoekstra
(74) *Attorney, Agent, or Firm* — Barclay Damon LLP; Daniel McGrath

(57) ABSTRACT

Disclosed is a device for transdermally detecting the concentration of one or more substances in a subject's bloodstream. The device includes a signal generation module arranged to generate microwave frequency signals at one or more discrete frequencies. The device also includes a sensor module comprising at least one microwave resonance sensor arranged to make contact with a subject's skin, the at least one microwave resonance sensor arranged to transmit microwave frequency signals generated by the signal generation module into the subject's body. The device also includes a signal processing module connected to the at least one microwave resonance sensor and arranged to: detect a resonance characteristic of the at least one microwave
(Continued)

| Composition | Amplitude Response T below threshold Tn at selected Frequency Fn | | | |
|---|---|---|---|---|
| | F1 | F2 | F3 | F4 |
| Blood+Ethanol (10mg) | X | | | |
| Blood+Ethanol (20mg) | X | | | |
| Blood+Ethanol (40mg) | X | | | |
| Blood+Ethanol (80mg) | X | X | | |
| | | | | |
| Blood+Cocaine metabolite | | | | X |
| Blood+THC (0.25mg) | | | X | X | resonance sensor, and process the resonance characteristic to determine the concentration of one or more substances in a subject's bloodstream.

16 Claims, 11 Drawing Sheets

(56)                    References Cited

U.S. PATENT DOCUMENTS

| | | | |
|---|---|---|---|
| 2013/0289375 | A1 | 10/2013 | Fischer |
| 2016/0073923 | A1 | 3/2016 | Szczepaniak et al. |
| 2017/0231536 | A1 | 8/2017 | Bharj |
| 2019/0008422 | A1 | 1/2019 | Leath et al. |

FOREIGN PATENT DOCUMENTS

| | | | | | |
|---|---|---|---|---|---|
| KR | 20140017243 | A | | 2/2014 | |
| WO | WO-03003915 | A2 | * | 3/2003 | ......... A61B 5/14532 |
| WO | WO-2005015184 | A1 | * | 2/2005 | ......... A61B 5/14532 |
| WO | WO-2007140185 | A2 | * | 12/2007 | ......... A61B 5/14532 |
| WO | 2017089639 | A1 | | 11/2016 | |
| WO | WO-2017115361 | A1 | * | 7/2017 | ........... A61B 5/0002 |

* cited by examiner

102

101

102

101

302

301

302

301

TOP VIEW

SIDE VIEW

FRONT VIEW

600

| | Amplitude Response T below threshold Tn at selected Frequency Fn | | | |
|---|---|---|---|---|
| Composition | F1 | F2 | F3 | F4 |
| Blood+Ethanol (10mg) | X | | | |
| Blood+Ethanol (20mg) | X | | | |
| Blood+Ethanol (40mg) | X | | | |
| Blood+Ethanol (80mg) | X | X | | |
| | | | | |
| Blood+Cocaine metabolite | | | | X |
| Blood+THC (0.25mg) | | | X | X |

Fig 8

DEVICE FOR NON-INVASIVE SUBSTANCE DETECTION

CROSS-REFERENCE TO RELATED APPLICATIONS

This application is a U.S. national stage application under 35 U.S.C. 371 of co-pending International Application No. PCT/GB2021/051283, filed on May 26, 2021, and entitled "Device for non-invasive substance detection", which claims priority to United Kingdom Application No. 2008272.3, filed Jun. 2, 2020, the contents of each of which are incorporated herein by reference in their entirety for all purposes.

TECHNICAL FILED

The present invention relates to a device and associated method for transdermally detecting the concentration of one or more substances in a subject's bloodstream.

Detecting the concentration of substances in a subject's bloodstream is important in many situations. For example, in a medical context it can be desirable to detect the concentration in a subject's bloodstream of various biomarkers that are indicative of a health condition. Additionally, in law enforcement or regulatory health and safety contexts it can be desirable to detect the concentration of substances such as alcohol, cannabis or cocaine in a subject's bloodstream.

Current techniques for detecting the concentration of substances in a subject's bloodstream rely on invasive procedures where a blood sample is taken from a subject using a needle and the blood sample is sent to a laboratory for testing.

Such phlebotomy-based techniques have several disadvantages. They are typically slow because they require the blood sample to be sent to a laboratory, which is often at a different location to the place where the blood sample is taken. In such cases, it can take several days to receive blood test results. Additionally, phlebotomy techniques require specially trained healthcare staff, can be uncomfortable, and carry a small infection risk.

SUMMARY OF THE INVENTION

According to a first aspect of the invention, there is provided a device for transdermally detecting the concentration of one or more substances in a subject's bloodstream. The device comprises a signal generation module arranged to generate microwave frequency signals at one or more discrete frequencies. The device further comprises a sensor module. The sensor module comprises at least one microwave resonance sensor arranged to make contact with a subject's skin. The at least one microwave resonance sensor is arranged to transmit microwave frequency signals generated by the signal generation module into the subject's body. The device further comprises a signal processing module connected to the at least one microwave resonance sensor and arranged to: detect a resonance characteristic of the at least one microwave resonance sensor, and process the resonance characteristic to determine the concentration of one or more substances in a subject's bloodstream.

Optionally, the signal generation module is arranged to generate microwave frequency signals at two or more discrete frequencies.

Optionally, the signal generation module is arranged to selectively generate microwave frequency signals at a first discrete frequency followed by microwave frequency signals at one or more further discrete frequencies.

Optionally, the signal processing module is arranged to process a first resonance characteristic of at least one of the at least one microwave resonance sensor to determine whether said first resonance characteristic satisfies a first predetermined criteria, and to process a second resonance characteristic of at least one of at least one microwave resonance sensor to determine whether said second resonance characteristic satisfies a second predetermined criteria. The first and second resonance characteristics may be resonant characteristics of the same sensor or separate sensors if the device comprises a plurality of microwave resonance sensors.

Optionally, the first resonance characteristic is an amplitude response associated with a microwave frequency signal at a first discrete frequency, and the second resonance characteristic is an amplitude response associated with a microwave frequency signal at a second discrete frequency.

Optionally, the signal processing module is arranged to determine that the amplitude response at the first discrete frequency corresponds with a stored amplitude response at the first discrete frequency of at least one known composition.

Optionally, the signal processing module is arranged to determine that the amplitude response at the second discrete frequency corresponds with a stored amplitude response at the second discrete frequency of at least one known composition.

Optionally, each known composition comprises at least a first substance and an anolyte.

Optionally, each known composition comprises a predetermined concentration of said anolyte.

Optionally, the sensor module is arranged to receive a subject's extremity.

Optionally, the sensor module comprises an aperture that extends through the sensor module, and wherein the aperture is shaped to receive a subject's extremity.

Optionally, the at least one microwave resonance sensor is positioned on a surface of the sensor module adjacent to the aperture.

Optionally, the aperture is substantially O-shaped.

Optionally, the sensor module comprises a cut-out region adjacent to the aperture and arranged to enable the sensor module to deform when a subject's extremity is received within the sensor module.

Optionally, the sensor module comprises a first part and a second part shaped to receive a subject's extremity therebetween, and wherein the first part and the second part are connected by a hinge to enable movement of the first part relative to the second part.

Optionally, the sensor module is resiliently deformable.

Optionally, the sensor module comprises an elongate base surface that is arranged to make contact with a subject's extremity along a length of the subject's extremity.

Optionally, the one or more microwave resonance sensor is a planar sensor.

Optionally, the one or more microwave resonance sensor comprises a transmission antenna and a receiving antenna.

Optionally, the transmission antenna and the receiving antenna are arranged on a substrate.

Optionally, the substrate is flexible.

Optionally, the one or more microwave resonance sensor comprises a first transmission antenna arranged adjacent a first receiving antenna, and a second transmission antenna arranged adjacent a second receiving antenna.

Optionally, the first transmission antenna and the first receiving antenna are spaced from the second transmission antenna and the second receiving antenna in a plane parallel to the plane of the sensor.

Optionally, the one or more microwave resonance sensors are resonant hairpin sensors.

Optionally, the device further comprises a base unit.

Optionally, the signal generation module and the signal processing module are located within the base unit.

Optionally, the sensor module is attached to an outer surface of the base unit.

Optionally, the device further comprises a power source, wherein the power source is a battery located within the base unit.

Optionally, the at least one microwave resonance sensor is adapted to resonate at least at a first frequency and a second frequency, the second frequency being different from the first frequency.

Optionally, the sensor module comprises at least two microwave resonance sensors.

Optionally, a first of the at least two microwave resonance sensors is adapted to resonate at a first frequency to measure one or more first substances in a subject's bloodstream and a second of the at least two microwave resonance sensors is adapted to resonate at a second frequency to measure one or more second substances in a subject's bloodstream, wherein the first and second frequencies are different.

Optionally, the signal processing module is adapted to process the resonance characteristic to determine the concentration of one or more substances in a subject's bloodstream by comparing the resonance characteristic with a stored resonance characteristic indicative of a concentration of a substance in a subject's bloodstream.

Optionally, the signal processing module is adapted to process the resonance characteristic to determine the concentration of one or more substances in a subject's bloodstream by inputting the resonance characteristic into a neural network that is trained to identify a concentration of a substance in a subject's bloodstream.

Optionally, the device further comprises a control module, wherein the control module is arranged to send a command to the signal generation module to cause the signal generation module to generate microwave frequency signals at one or more discrete frequencies.

Optionally, the device is a point of care device.

Optionally, the device is arranged to detect the concentration in a subject's bloodstream of one or more of alcohol, tetrahydrocannabinol, cocaine, lactate, haemoglobin, sodium chloride, potassium chloride and urea.

Optionally, the resonance characteristic is determined based on signals transmitted and/or reflected by the at least one microwave resonance sensor.

Optionally, the signal generation module is arranged to generate at least one discrete microwave frequency signal at a frequency that is not less than 0.01 GHz and not greater than 15 GHz.

Optionally, the signal generation module is arranged to generate at least one discrete microwave frequency signal at a frequency that is not less than 0.01 GHz and not greater than 1 GHz, such as 786 MHz. Optionally, the signal generation module is arranged to generate at least one discrete microwave frequency signal at a frequency that is not less than 2.2 GHz and not greater than 2.7 GHz, and optionally not greater than 2.4 GHz. One or more discrete frequencies selected from these ranges is particularly suitable for determining the presence and concentration of ethanol in blood.

Optionally, the signal generation module is arranged to generate at least one discrete microwave frequency signal at a frequency that is not less than 7.20 GHz and not greater than 7.55 GHz. One or more discrete frequencies selected from this range is particularly suitable for determining the presence and concentration of ethanol in blood.

Optionally, the signal generation module is arranged to generate at least one discrete microwave frequency signal at a frequency that is not less than 1 GHz and not greater than 2 GHz, and preferably not less than 1.3 GHz and not greater than 1.5 GHz, such as at 1.31 GHz or 1.5 GHz. One or more discrete frequencies selected from these ranges is particularly suitable for determining the presence and concentration of Hydroxy-THC in blood.

Optionally, the signal generation module is arranged to generate at least one discrete microwave frequency signal at a frequency that is not less than 250 MHz and not greater than 260 MHz, such as at 250 MHz. One or more discrete frequencies selected from this range is particularly suitable for determining the presence and concentration of Norcocaine Hydro Chloride in blood.

Optionally, the signal generation module is arranged to generate at least one discrete microwave frequency signal at a frequency that is not less than 4 GHz and not greater than 4.2 GHz, such as at 4.12 GHz. One or more discrete frequencies selected from this range is particularly suitable for determining the presence and concentration of Cannabinol Solutions in blood.

Optionally, the signal generation module is arranged to generate at least one discrete microwave frequency signal at a frequency that is not less than 8 GHz and not greater than 11 GHz. One or more discrete frequencies selected from this range is particularly suitable for determining the presence and concentration of the cocaine metabolite ecgonine methyl ester in blood.

Optionally, the signal generation module is arranged to generate at least one discrete microwave frequency signal at a frequency that is not less than 25 MHz and not greater than 1.7 GHz. One or more discrete frequencies selected from this range is particularly suitable for determining the presence and concentration of lactate in blood.

Optionally, the signal generation module is arranged to generate at least one discrete microwave frequency signal at a frequency that is not less than 60 MHz and not greater than 1 GHz. One or more discrete frequencies selected from this range is particularly suitable for determining the presence and concentration of haemoglobin in blood.

Optionally, the signal generation module is arranged to generate at least one discrete microwave frequency signal at a frequency which corresponds with a resonance frequency of at least one known composition. The known composition may comprise blood having a predetermined concentration of at least one of alcohol, tetrahydrocannabinol, cocaine, lactate, haemoglobin, sodium chloride, potassium chloride and urea.

According to a second aspect of the invention, there is provided a method of transdermally detecting the concentration of one or more substances in a subject's bloodstream. The method comprises: generating microwave frequency signals at one or more discrete frequencies; transmitting, via at least one microwave resonance sensor of a sensor module, the microwave frequency signals into the subject's body; detecting a resonance characteristic of the at least one microwave resonance sensor; and processing the resonance characteristic to determine the concentration of one or more substances in the subject's bloodstream.

Optionally, the step of generating microwave frequency signal at one or more discrete frequencies comprises:

generating a first microwave frequency signal at a first discrete frequency, and generating a second microwave frequency signal at a second discrete frequency.

Optionally, the step of processing the resonance characteristic to determine the concentration of one or more substances in the subject's bloodstream comprises:

determining that a resonance characteristic of at least one of said at least one microwave resonance sensor satisfies a first predetermined criteria; and determining that a resonance characteristic of at least one of said at least one microwave resonance sensor satisfies a second predetermined criteria.

Optionally, the step of determining that a resonance characteristic of at least one of said at least one microwave resonance sensor satisfies a first predetermined criteria comprises:

comparing an amplitude response of a at least one of said at least one microwave resonance sensor against a stored amplitude response associated with at least one known composition comprising a concentration of one or more substances in blood.

Optionally, the step of determining that a resonance characteristic of at least one of said at least one microwave resonance sensor satisfies a second predetermined criteria comprises:

comparing an amplitude response of at least one of said at least one microwave resonance sensor against a stored amplitude response associated with at least one known composition comprising a concentration of one or more substances in blood.

Optionally, the signal generation module is arranged to generate at least one discrete microwave frequency signal at a frequency that is not less than 0.01 GHz and not greater than 15 GHz, such as a frequency in accordance with a frequency that may optionally be generated by the signal generation module of the first aspect of the invention.

Optionally, the at least one discrete microwave frequency signal is at a frequency which corresponds with a resonance frequency of at least one known composition. The known composition may comprise blood having a predetermined concentration of at least one of alcohol, tetrahydrocannabinol, cocaine, lactate, haemoglobin, sodium chloride, potassium chloride and urea.

Advantageously, certain aspects of the invention provide a device for transdermally detecting the concentration of one or more substances in a subject's bloodstream that can accurately detect the concentration of substances in a subject's bloodstream.

Advantageously, certain aspects of the invention provide a device for transdermally detecting the concentration of one or more substances in a subject's bloodstream that is compact, reliable, and cost effective to manufacture. In particular, providing a signal generation module arranged to only generate signals at discrete frequencies (i.e. as opposed to generating signals along a continuous frequency "sweep") means that the electronics of the device can be simplified. It can also make the device easier to calibrate because the signals generated by the signal generation module are predictable.

Advantageously, certain aspects of the invention provide a device for transdermally detecting the concentration of one or more substances in a subject's bloodstream that can operate in a non-invasive (transdermal) manner (that is, without requiring a needle to be inserted through the skin).

Advantageously, certain aspects of the invention provide a device for transdermally detecting the concentration of one or more substances in a subject's bloodstream that is portable, convenient, comfortable for a subject and that can provide rapid test results. This can make the device particularly suited to use at a point of care or point of testing.

Various further features and aspects of the invention are defined in the claims.

BRIEF DESCRIPTION OF THE DRAWINGS

Embodiments of the present invention will now be described by way of example only with reference to the accompanying drawings where like parts are provided with corresponding reference numerals and in which:

FIG. 8 shows a table used to determine the presence of an anlyte in a composition.

DETAILED DESCRIPTION

Figure 1A:
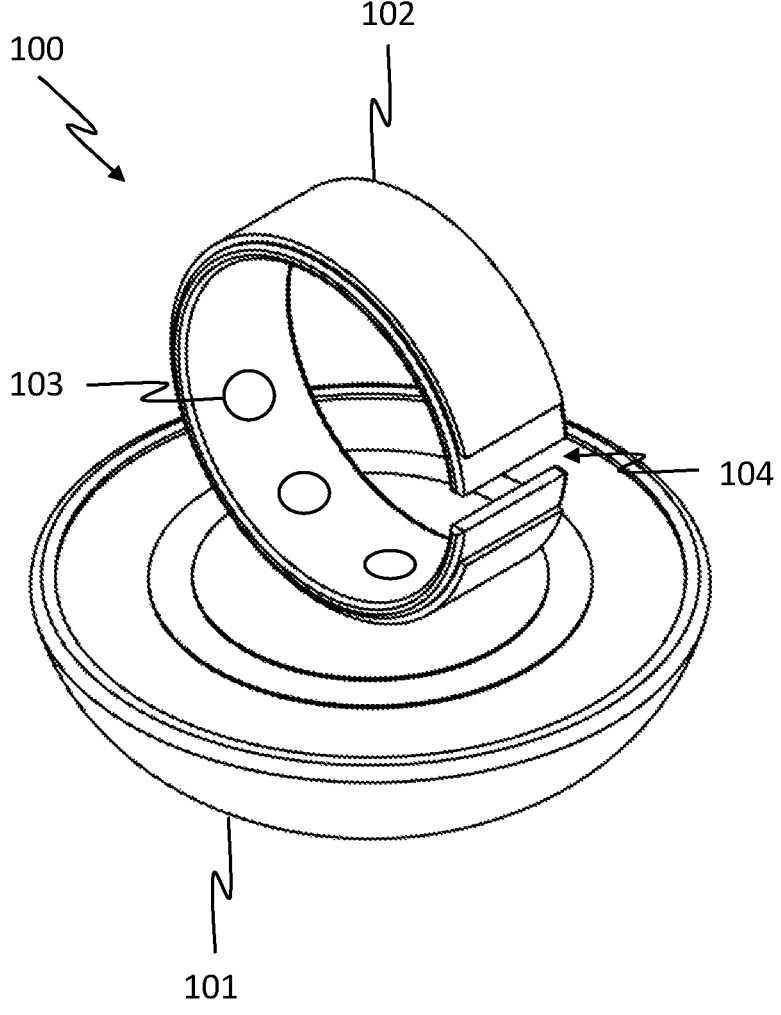
FIG. 1A shows a device for transdermally detecting the concentration of one or more substances in a subject's bloodstream in accordance with certain embodiments of the invention.

FIG. 1A shows a device 100 for transdermally detecting the concentration of one or more substances in a subject's bloodstream in accordance with embodiments of the invention.

The device 100 is arranged to transmit microwave frequency signals into a subject's body through the skin via microwave resonance sensors and based on a resonance characteristic of the sensors, detect the concentration of substances such as alcohol, tetrahydrocannabinol, cocaine, lactate, haemoglobin, sodium chloride, potassium chloride, and urea in the subject's bloodstream. It will be understood that in certain embodiments, the concentration of other suitable substances can also be detected by the device 100.

It will be understood that the substances that can be detected by the device 100 include molecules naturally occurring in the body such as biomarkers indicative of a biological state of the body, and molecules that are not naturally occurring in the body such as psychoactive drugs. The substances that can be detected are also referred to herein collectively as analytes.

Microwave resonance sensing is a sensing technique that can be used to detect changes in the dielectric properties of a material to which a microwave resonance sensor is applied. Changes in the dielectric properties of a material can be caused by the presence and concentration of certain substances in the material. Changes in the dielectric properties of a material can be detected by a microwave resonance sensor as changes in the resonance characteristics of the sensor (typically determined based on the magnitude and/or phase of signals that are transmitted and/or reflected by the sensor). Typically, a microwave resonance sensor is designed so that it has a resonant frequency close to a resonant frequency of a substance to be detected.

The device 100 is a standalone portable device intended for use at a location where testing takes place such as at a medical point of care or workplace testing facility.

The device 100 includes a base unit 101 and a sensor module 102.

The device 100 typically includes various further components, which are located within the base unit 101, including a control module, a signal generation module, a signal processing module and a battery and/or mains power connector as described in more detail with reference to FIG. 2.

The sensor module 102 includes a substantially ring-shaped body. An inner surface of the body defines an O-shaped aperture that extends through the sensor module 102 and is shaped to receive a subject's extremity such as a finger, wrist, or leg.

In this embodiment, the sensor module 102 includes three microwave resonance sensors 103. The sensors 103 are located on a surface of the body of the sensor module 102 so that when a subject's extremity is received within the aperture, the sensors 103 make contact with the skin of the subject's extremity.

The sensors 103 are arranged to transmit microwave signals into a subject's extremity. In certain embodiments, the sensors 103 are hairpin sensors that substantially correspond with the sensors described herein with reference to FIG. 5.

In certain embodiments, each sensor 103 is a planar sensor comprising a transmission antenna and a receiving antenna arranged on a substrate, such as a PTFE substrate. The substrate may be flexible. The antennas are themselves planar and extend in substantially the same plane as each other. The antennas may be printed onto the underlying substrate. The transmission antenna has an electrical input port for connection to a signal generation module and the receiving antenna has an electrical output port for connection to a signal processing module. In certain embodiments, each sensor comprises first and second transmission antennas and corresponding first and second receiving antennas.

Sensor may be a microwave resonator, such as a transverse electromagnetic resonator.

The sensors 103 are spaced apart around the inside surface of the body. As discussed in more detail herein, in certain embodiments, each sensor 103 is suited to detecting one or more substances of a certain range of substances based on the resonant frequency of the sensor being the same as or similar to the resonant frequency of a substance or range of substances to be detected. Alternatively, in certain embodiments the sensors 103 are the same or similar and are provided for redundancy in case one or more of the sensors is not operational or is not in contact with the subject's extremity.

Typically, the sensor module 102 is resiliently deformable. In this way, when a subject's extremity is inserted into the sensor module 102, the sensor module 102 can deform to enable the sensor module 102 to fit a range of sizes of extremity and still ensure contact is made between the sensors 103 and the subject's skin.

The sensor module 102 includes a cut-out region 104. The cut-out region 104 extends through the body of the sensor module 104 and is arranged to enable the sensor module 102 to further deform when a subject's extremity is received within the sensor module 102.

Typically, the body of the sensor module 102 is composed of a resiliently deformable material such as plastic.

As noted, the device 100 includes three sensors. However, it will be appreciated that in other embodiments, one sensor, two sensors, or more than three sensors can be provided.

Figure 1B:
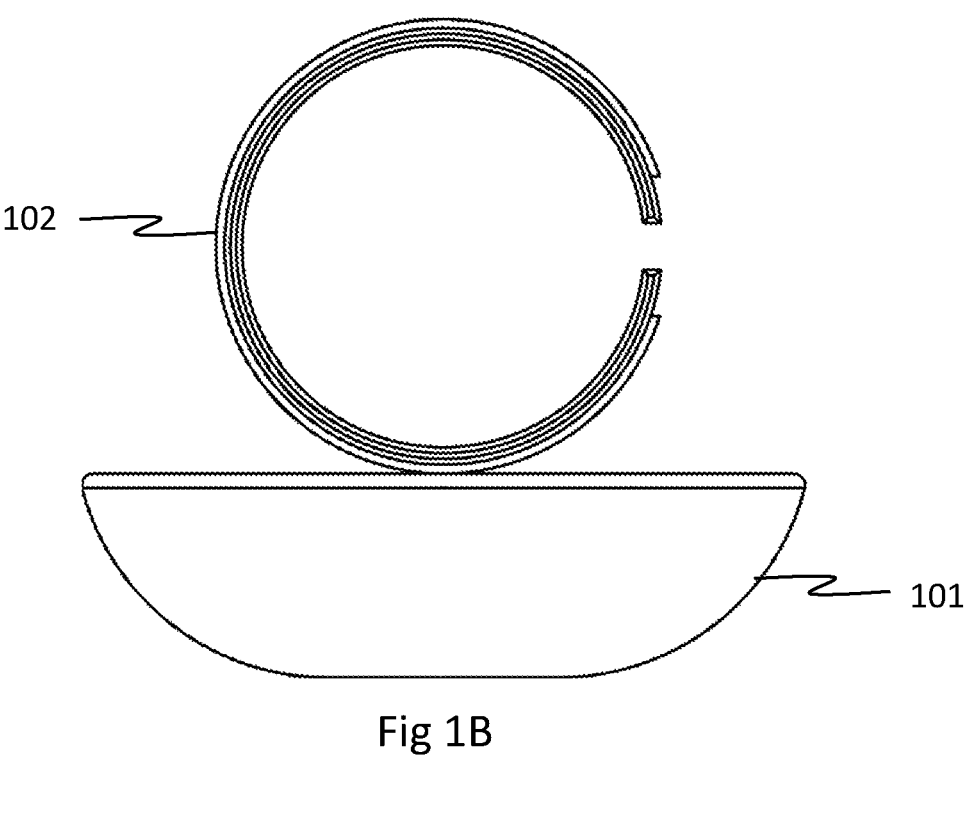
FIG. 1B provides a front view of the device of FIG. 1A.
Figure 1C:
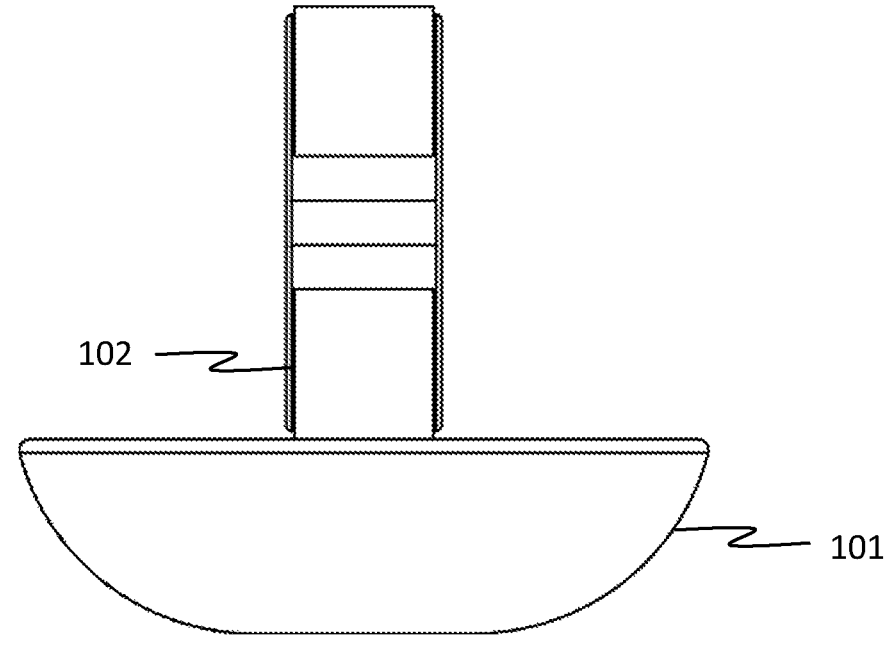
FIG. 1C provides a side view of the device of FIG. 1A.

FIG. 1B provides a front view of the device of FIG. 1A and FIG. 1C provides a side view of the device of FIG. 1A.

Figure 2:
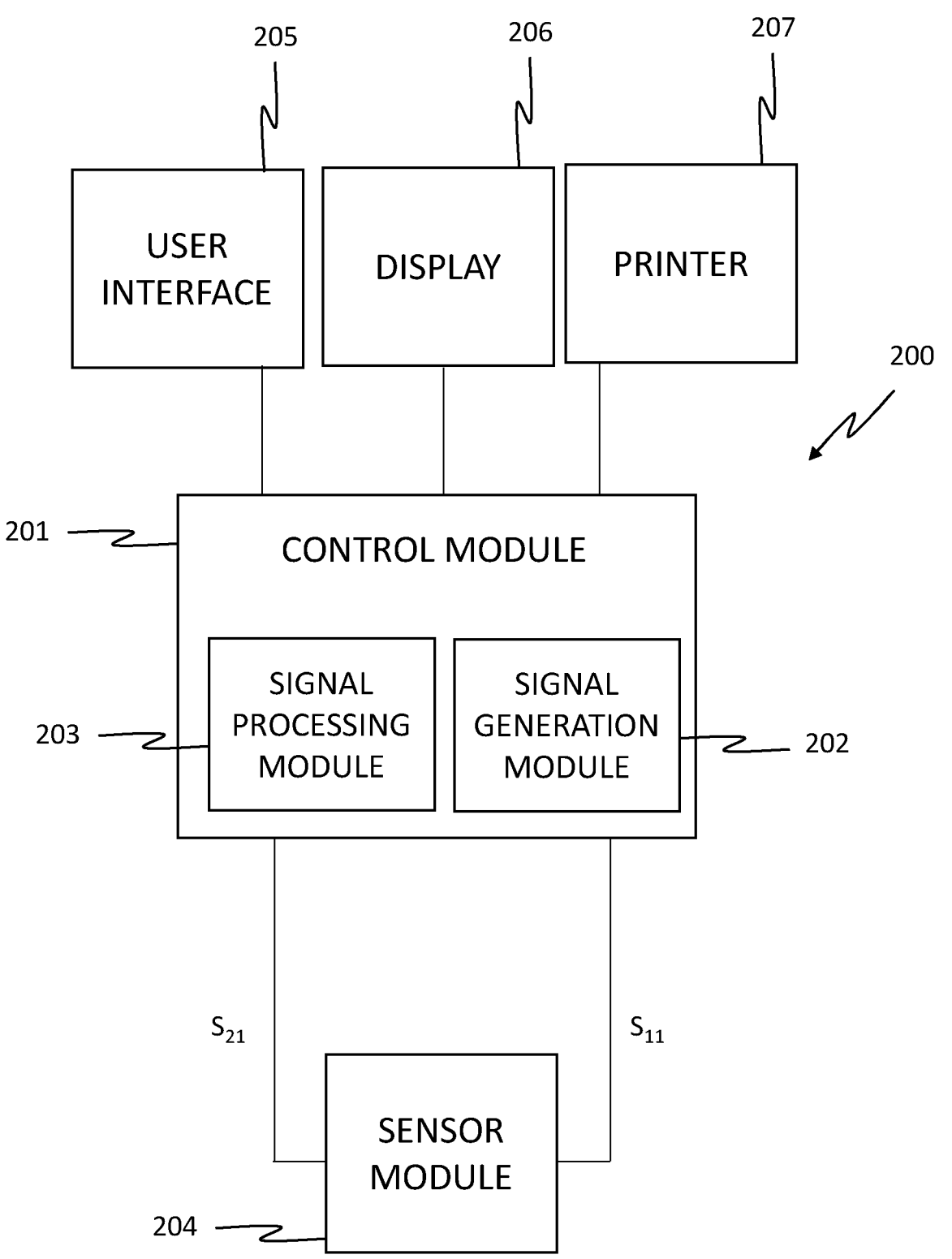
FIG. 2 is a simplified schematic diagram of a device for transdermally detecting the concentration of one or more substances in a subject's bloodstream in accordance with certain embodiments of the invention.

FIG. 2 is a simplified schematic diagram of a device for transdermally detecting the concentration of one or more substances in a subject's bloodstream in accordance with certain embodiments of the invention.

The device 200 includes a control module 201. The control module 201 includes a signal generation sub-module 202 and a signal processing sub-module 203. The device 200 also includes a sensor module 204, a user interface 205, a display 206, and a printer 207.

The control module 201 is arranged to control the operation of other modules of the device 200.

The user interface 205 is arranged to receive inputs from a user of the device 200 to enable the user to operate the device 200. For example, the user interface 205 can include one or more buttons that the user can press to cause the device 200 to perform various actions (e.g. device on/off, start/stop test, print test results etc.).

The display 206 is arranged to display information to a user of the device 200 such as current device status, battery level and test results. It will be understood that any suitable type of display can be used. For example, an LCD display can be used.

The printer 207 is arranged to receive print data and to print a document based on the received print data. In certain embodiments, the document printed by the printer can provide the results of a test performed by the device 200 (e.g. the concentration of a substance in a subject's bloodstream).

The sensor module 204 comprises a microwave resonance sensor. In certain embodiments, the sensor is a hairpin sensor such as the sensor described with reference to FIG. 5. The sensor is arranged to make contact with a user's skin and to transmit microwave signals generated by the signal generation module 202 into the user's body.

The sensor of the sensor module 204 is connected to the signal generation and signal processing modules 202 203 such that the signal generation module 202 can apply signals to the sensor and the signal processing module 203 can measure a resonance characteristic of the sensor in response to the applied signals. Typically, the resonance characteristic of the sensor is determined based on signals transmitted and/or reflected by the sensor in response to the signals applied to the sensor by the signal generation module 202.

In certain embodiments, the resonance characteristic of the sensor comprises data corresponding to the magnitude of signals transmitted and/or reflected by the sensor in response to each discrete signal applied to the sensor by the signal generation module 202.

The signal generation module 202 is arranged to receive a command from the control module 201 and responsive thereto, to generate microwave signals at one or more discrete frequencies and apply the signals to the sensor of the sensor module 204.

The signal generation module 202 includes a first oscillator circuit that is arranged to generate an oscillating signal at a single predetermined frequency in the microwave frequency range.

The signal generation module 202 can include one or more further oscillator circuits which are each arranged to generate an oscillating signal at a further single predetermined frequency in the microwave frequency range.

In this way, the signal generation module 202 is arranged to only generate signals at discrete frequencies. That is, the signal generation module 202 is not arranged to generate a frequency "sweep" over a range of frequencies but rather as one or more discrete frequencies.

Advantageously, this means that the electronics of the signal generation module 202 can be simplified compared with the electronics needed to generate a continuous frequency "sweep". This can provide a smaller, more reliable, cheaper to manufacture and less complex device. It can also make the device easier to calibrate to perform reliable tests because the signals generated by the signal generation module are predictable. For example, in certain embodiments the signal generation module 202 can use electronics similar to a signal generator used in a mobile phone.

In certain embodiments, the signal generation module 202 is arranged to generate signals at approximately 2.6 GHz. Signals at or close to this frequency can be particularly useful to detect the concentration of alcohol in a subject's bloodstream. It will be understood that other frequencies of interest can be used to detect the concentration of other substances in a subject's bloodstream.

The signal generation module 202 is electrically connected to the sensors of the sensor module 204 such that signals generated by the signal generation module 202 are applied to the sensor of the sensor module 204.

Where the signal generation module 202 includes more than one oscillator circuit, responsive to a command from the control module 201 to generate signals, the signal generation module 202 is arranged to generate a first frequency signal from the first oscillator circuit, followed by subsequent signals from any further oscillator circuits in turn.

Figure 6:
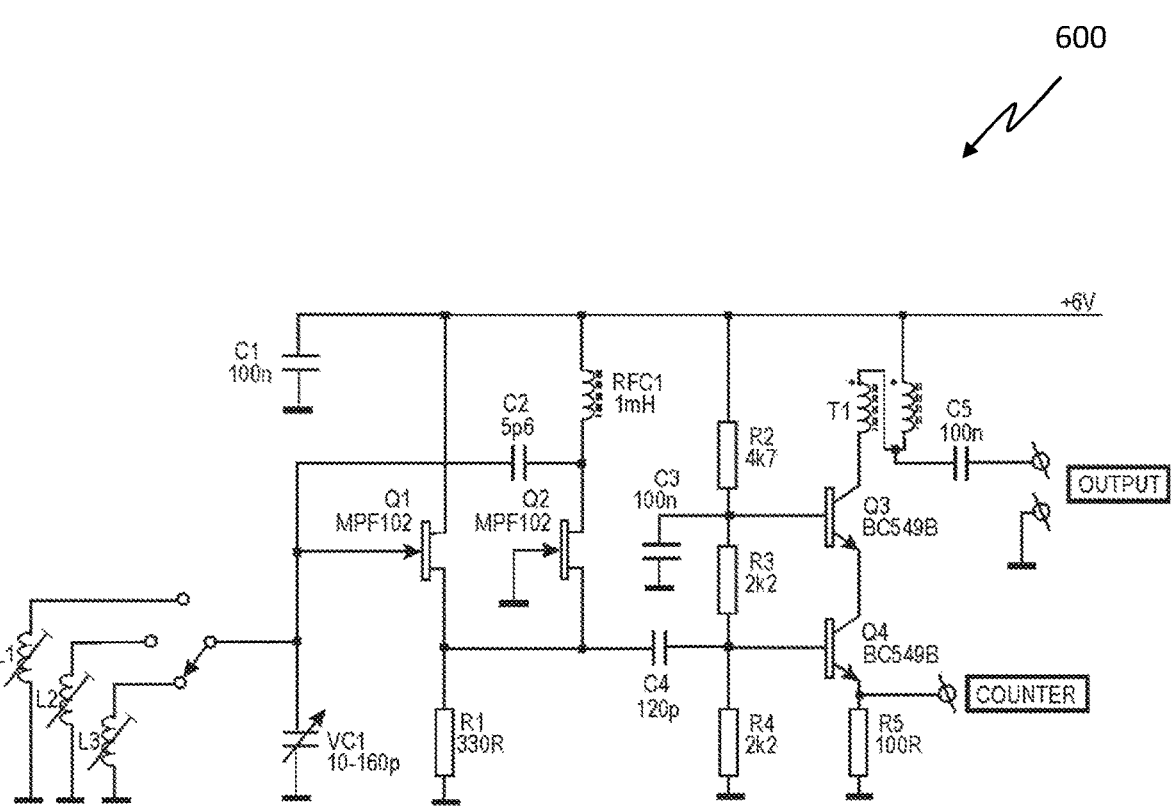
FIG. 6 provides a circuit diagram of a signal generator circuit of a type that can be used as part of a signal generation module.

FIG. 6 provides a circuit diagram of a signal generator circuit 600 of a type that can be provided as part of the signal generation module 202.

The signal processing module 203 is arranged to detect a resonance characteristic of the sensor as described herein. The signal processing module 203 is further arranged to process the resonance characteristic to determine the concentration of one or more substances in the subject's bloodstream.

In this embodiment, the sensor of the sensor module 204 includes two ports and the signal processing module 203 is connected to the sensor to measure a resonance characteristic based on both the signal reflected ($S_{11}$) and transmitted ($S_{21}$) by the sensor.

In embodiments where the signal generation module 202 generates signals at two or more discrete frequencies (i.e. via two or more oscillator circuits), the signal processing module 203 is arranged to receive the transmitted and reflected signals for each signal generated by the signal generation module 202 in turn.

The signal processing module 203 includes circuitry to convert the received signal into a form suitable for further processing. Typically, the signal processing module 203 includes an analogue to digital converter (ADC) arranged to convert the received signals into a digital format for further processing to determine the resonance characteristic as described herein.

In embodiments where the signal generation module 202 generates signals at two or more discrete frequencies in turn, the signal processing module 203 combines data from each signal to construct a resonance characteristic for the sensor. In such embodiments, the resonance characteristic of the sensor comprises data corresponding to the magnitude of signals transmitted and reflected by the sensor at two or more discrete frequencies in response to the signals applied to the sensor by the signal generation module 202.

The signal processing module 203 is arranged to compare the determined resonance characteristic with one or more stored resonance characteristics representing a known concentration of a substance in a subjects bloodstream. Based on this comparison (for example, by identifying a closest match), the concentration of a substance in a subject's bloodstream can be determined.

Alternatively, or additionally, the signal processing module 203 includes a trained neural network. In such embodiments, the resonance characteristic can be passed into the trained neural network. The neural network outputs an estimated concentration of a substance in a subject's bloodstream.

The control module 201 includes components that perform data processing and storage. The control module is arranged to control the operation of other modules of the device 200.

The control module 201 is arranged to control the signal generation module 202 by sending a command to the signal generation module 202 to cause the signal generation module 202 to generate microwave frequency signals at one or more discrete frequencies.

The control module 201 is arranged to control the display 205, by sending a display command to the display 205 to cause the display 205 to present information such as the current status of the device 200, or the results of a test performed by the device 200 (e.g. the concentration of a substance in a subject's bloodstream).

The control module 201 is arranged to control the printer 207, by sending a print command to the printer 207 to cause the printer 207 to print a document, for example a document providing the results of a test performed by the device 200 (e.g. the concentration of a substance in a subject's bloodstream).

The control module 201 is arranged to receive signals from other modules of the device 200, including: from the user interface 204, which sends to the control module 201 signals based on user inputs to the user interface. For example, where the user interface 204 includes physical buttons (e.g. on/off, start/stop test, print results buttons), the control module 201 receives from the user interface 204 signals corresponding to one or more buttons of the user interface 204 pressed by a user.

The device 200 will now be described in use during a test to determine the concentration of a substance in a human subject's bloodstream.

First, a subject's extremity is placed in contact with the sensor of the sensor module 204 so that the subject's skin is in contact with the sensor. An operator of the device 200

(which may or may not be the subject) interacts with the user interface 205 by pressing one or more buttons to initiate a test.

The control module 201 receives the input from the user interface and initiates a test procedure.

The control module 201 sends a command to the signal generation module 202 to begin a test. Responsive to the command, the signal generation module 202 generates and applies a signal at a first frequency to the sensor and repeats this for one or more further discrete frequencies in turn.

The signal processing module 203 receives signals from the sensor and determines a resonance characteristic of the sensor.

The signal processing module 203 compares the resonance characteristic with stored resonance characteristic data to determine the concentration of a substance in a subject's bloodstream, for example based on a closest matching stored resonance characteristic. Alternatively or additionally, the signal processing module inputs the resonance characteristic into a trained neural network which outputs an estimated concentration.

The test results can then be stored in internal storage of the device 200. The control module 200 can send a command to the display 206 to display the test results on the display 206. The control module 201 can also send a command to the printer 207 to print the test results.

Figure 7:
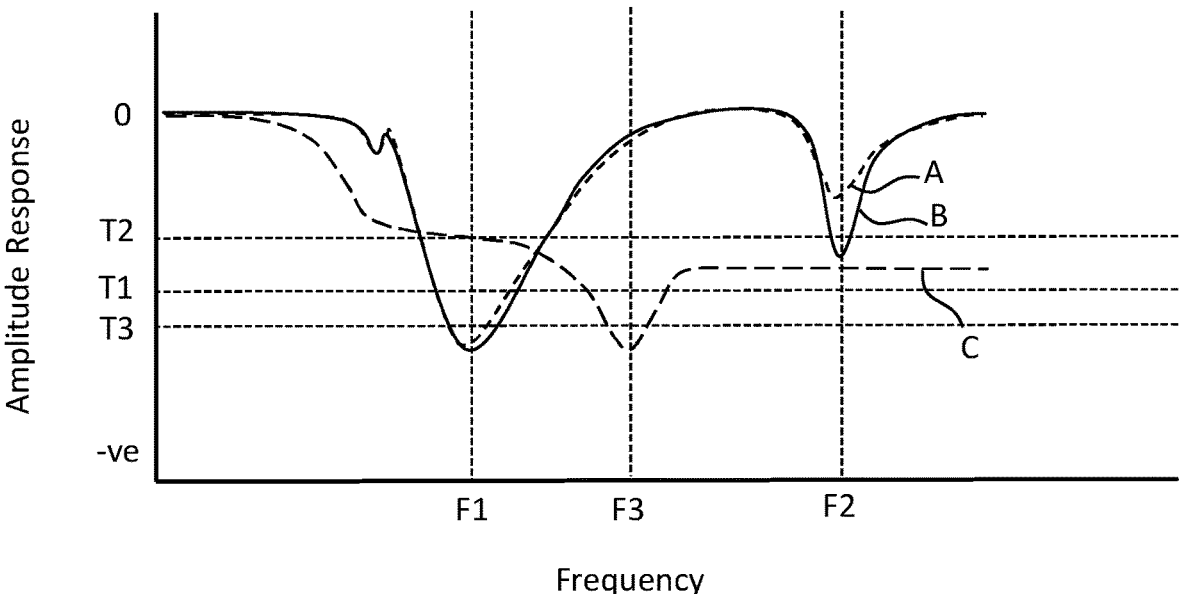
FIG. 7 shows a graphical representation showing an amplitude response against frequency for a sensor.

FIG. 7 is a graphical representation showing an amplitude response (i.e. resonance characteristic) against frequency for a sensor in relation to a microwave signal transmitted by the sensor for different compositions, such as blood having a particular concentration of an analyte. The representation is for illustrative purposes only and is not intended to represent actual amplitude responses.

By way of example, composition A could be blood having 40 mg/dl of ethanol concentration. Composition B could be blood having 80 mg/dl of ethanol concentration and composition C could be blood having 0.25 mg/ml of Hydroxy-THC concentration.

In order to determine the presence and concentration of an analyte within the blood, the signal generation module 202 generates and applies a signal at a first frequency F1 to at least one sensor 103. The signal received by the sensor 103 is then processed by the signal processing module 203 to determine an amplitude response.

The amplitude response is then compared against stored amplitude response thresholds. FIG. 8 provides an illustration of how an amplitude response below a predetermined threshold at a particular frequency F1, F2, F3, F4, Fn may be correlated with one or more predetermined compositions based on the responses shown in FIG. 7. If the amplitude response for a particular composition is below a threshold value Tn at a selected frequency Fn, this is indicated by an 'X'. It will be appreciated that FIG. 7 provides illustrative example of only selected compositions shown in FIG. 8.

In the present example, if the amplitude response at frequency F1 is below a predetermined threshold T1, it can be determined that the composition may be blood with an ethanol concentration between 10 mg and 80 mg.

In order to narrow down the possible composition candidates, for example, to determine the actual concentration of ethanol, the signal generation module 202 then generates and supplies a signal at a second frequency F2 to the sensor 103. The signal received by the sensor 103 is then processed by the signal processing module 203 to determine an amplitude response.

The amplitude response is compared against the stored amplitude response thresholds for the candidate compositions (i.e. blood with an ethanol concentration between 10 mg and 80 mg). If the amplitude response for the composition at frequency F2 is below a predetermined threshold T2, as indicated in the table shown in FIG. 8, it can be determined that the composition being assessed is blood with an ethanol concentration of 80 mg (i.e. the amplitude response at both F1 and F2 can be determined to most closely correspond with composition B shown in FIG. 7).

It will be appreciated that an amplitude response at a particular frequency can be compared against multiple thresholds that correspond to different concentrations of an analyte in order to determine possible candidates.

If the amplitude response at frequency F1 is above the predetermined threshold T1, it can be determined that the composition is not blood with an ethanol concentration between 10 mg and 80 mg. The amplitude response of the sensor 103 at a different selected frequency could then be used to further refine possible candidates. For example, if an amplitude response at frequency F3 is below threshold T3, it can be determined that the composition being assessed is blood with 0.25 mg/ml of Hydroxy-THC (i.e. composition C).

In this manner, suitable candidates can be selected and refined by a process of eliminating other candidates using selected frequencies. Each successive frequency may be selected arbitrarily, in accordance with a set procedure or based on the possible candidates that remain after previous steps.

The discrete frequencies for each anolyte are a frequency which is not less than 0.01 GHz and not greater than 15 GHz, and specifically may be as follows:

Ethanol: 0.01 GHz-1 GHz; 2.2 GHz-2.2 GHz

Ethanol: 7.20 GHz-7.55 GHz

Hydroxy-THC: 1 GHz-2 GHz

Norcocaine Hydro Chloride: 250 MHz-260 MHz, 250 MHz

Cannabinol Solutions: 4 GHz-4.2 GHz, 4.12 GHz

Ecgonine Methyl Ester: 8 GHz-11 GHz

In this embodiment, the signal generation module 202 and the signal processing module 203 are sub-modules of the control module 201. It will however be appreciated that in certain embodiments, the signal generation module 203 and/or the signal processing module 203 can be provided separate from the control module 201. Further, in certain embodiments, the signal generation module 202 and the signal processing module 203 can be provided as a single module providing the functionality of both modules. In such embodiments, the signal generation module 202 and signal processing module 203 form a single signal generation and processing module.

In certain embodiments, the device 200 includes a battery to provide a source of power to the electronic components of the device 200. In such embodiments, the device may be configured to be a wearable device. It will be understood that the device 200 could be provided with other suitable power sources. It will further be understood that alternatively or additionally to including a battery, the device 200 can include a mains power connector for connected the device 200 to a mains electricity source.

In certain embodiments, the sensor module 204 includes one or more further microwave resonance sensors. In such embodiments, each sensor can be operated in turn as described above.

Such further sensors can be identical or substantially correspond with the first sensor. This can provide redundancy in case the first sensor is not operational or not in contact with the subject's skin.

Alternatively, such further sensors can be different to the first sensor. For example, the further sensors can have different physical dimensions that make them suited to detecting the concentration of different substances (e.g. based on the resonant frequency of the sensor corresponding with the resonant frequency of the substance to be detected).

Typically, a sensor is used which is capable of emitting and detecting microwaves over a relatively narrow range of frequencies that incorporates the resonant frequencies associated with an analyte to be detected.

It will be understood that in certain embodiment, the device 200 can be provided with either a printer or a display.

In certain embodiments, the signal generation module 202 is arranged to generate microwave frequency signals at two, three, four, five, six or more than six discrete frequencies (via respective oscillator circuits).

Figure 3A:
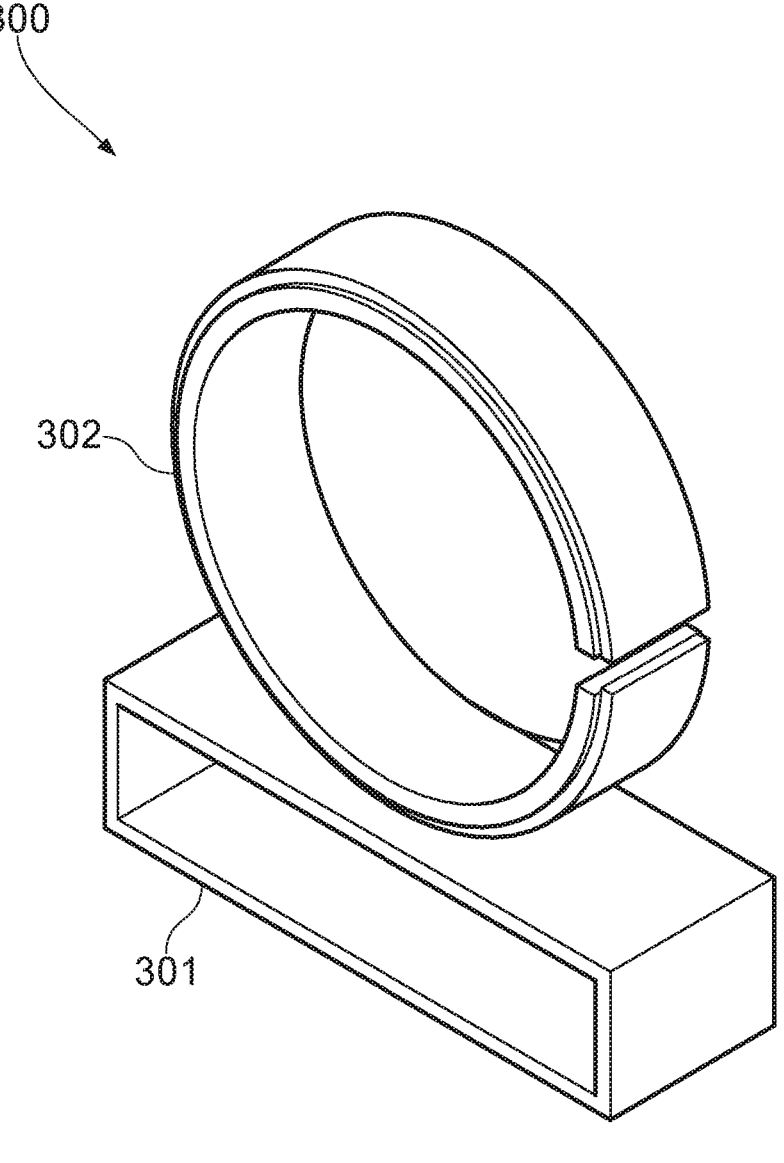
FIG. 3A shows a device for transdermally detecting the concentration of one or more substances in a subject's bloodstream in accordance with further embodiments of the invention.

FIG. 3A shows a simplified view of a device 300 in accordance with further embodiments of the invention. The device 300 substantially corresponds with the device of FIG. 1 except as otherwise described and depicted.

The device 300 includes a base unit 301 and a sensor module 302. In contrast with the device of FIG. 1, the base unit 301 has a substantially rectangular cross section.

Figures 3B, 3C:
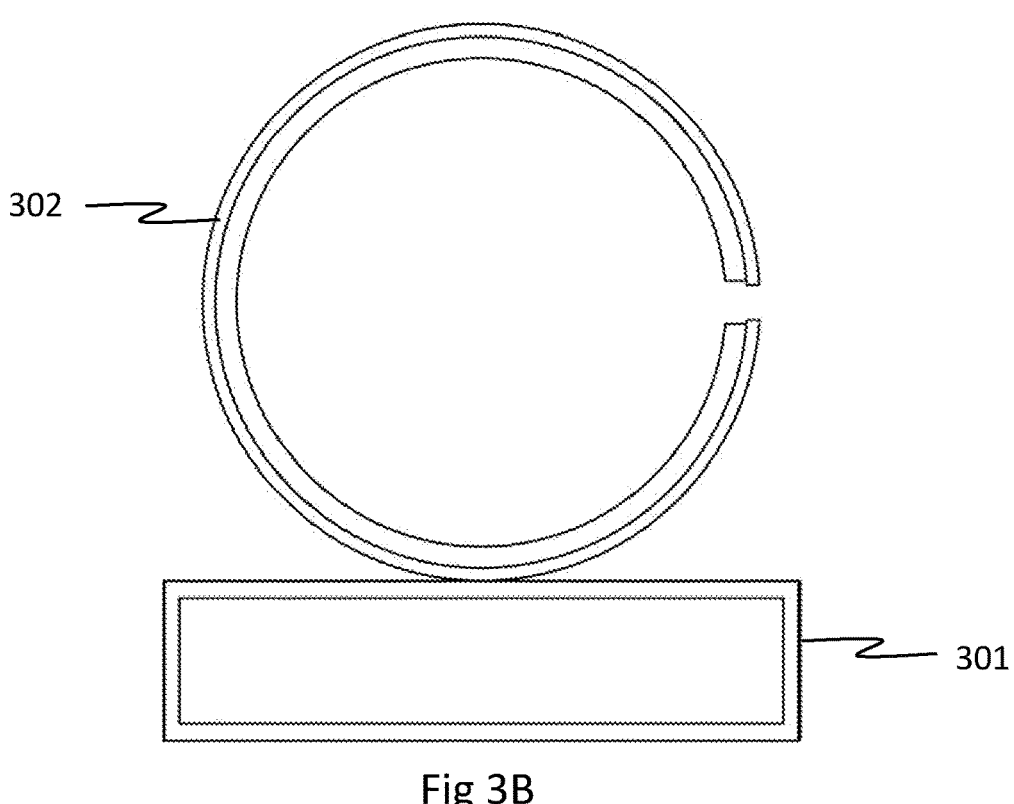
FIG. 3B provides a front view of the device of FIG. 3A.
FIG. 3C provides a side view of the device of FIG. 3A.

FIG. 3B provides a front view of the device of FIG. 3A and FIG. 3C provides a side view of the device of FIG. 3A.

Figure 4A:
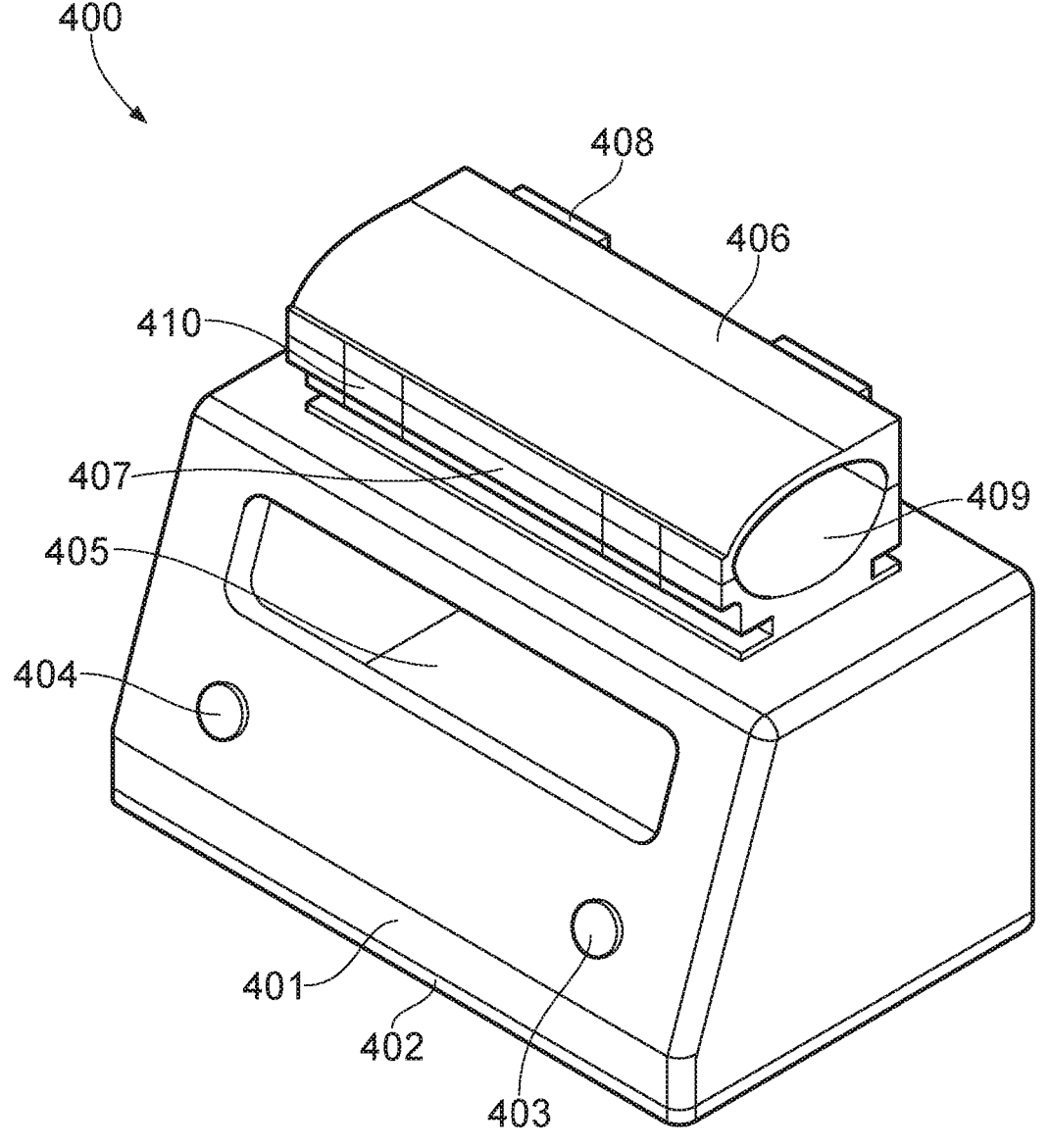
FIG. 4A shows a device for transdermally detecting the concentration of one or more substances in a subject's bloodstream in accordance with further embodiments of the invention.

FIG. 4A shows a device 400 in accordance with a further embodiment of the invention. The device 400 substantially corresponds with the device described with reference to FIG. 1 except as otherwise described and depicted.

The device 400 includes a base 401 with an outer cover 402.

Typically, the device 400 includes a control module, signal generation and processing modules and a battery located within the base 401 (not shown).

The device 400 includes first and second buttons 403 404 located on an outer surface of the base 401. The buttons 403 404 can be used to operate the device 400. The buttons 403 404 together form the device user interface.

The device 400 includes a display 405 located on an outer surface of the base 401. The display 405 is arranged to display information to a user of the device 400. It will be understood that any suitable type of display can be used. For example, an LCD display can be used.

The device 400 includes a sensor module. The sensor module in this embodiment includes an upper part 406 and a lower part 407. The lower part 407 is secured to the base 401. The upper part 406 and the lower part 407 are secured together via a hinge 408. The hinge 408 allows movement of the upper part 406 relative to the lower part 407.

The upper and lower parts 406 407 are shaped so that when they are brought together, they form a region 409 that is shaped to receive a subject's extremity. In this embodiment, the upper and lower parts 406 407 are shaped to receive a subject's arm and the lower part 407 includes an elongate base surface arranged to support the arm along the length of the arm.

The sensor module includes one or more microwave resonance sensors. Typically, the microwave resonance sensors are located on the lower part 407 of the sensor module so that they make contact with a subject's skin when the subject's extremity is rested on the lower part 407.

The sensor module includes a fastener 410. The fastener 410 is arranged to secure the upper and lower parts 406 407 together to prevent movement therebetween. In certain embodiments, the fastener 410 is a velcro fastener.

In use, the upper part 406 is opened relative to the lower part 407 via the hinge 408. A subject places their arm along the length of the lower part 407. The upper part 406 is then moved towards the lower part 407 and secured to the lower part via the fastener 410. This ensures that the subject's skin is in contact with the microwave resonance sensor(s) of the sensor module.

A test is then performed by the device to determine the concentration of a substance in the subject's bloodstream as described herein. The results of the test can be displayed on the display 405.

Advantageously, the device 400 provides a reliable and convenient means by which to receive a subject's extremity to perform a test. In particular, the movable upper part 406 and fastening ensures that the subject's extremity is correctly positioned in contact with the microwave resonance sensors of the device 400. This can improve the reliability of tests performed by the device 400.

Advantageously, the device 400 is a portable device that can be used at a point of care or point of testing.

In certain embodiments, the sensor(s) can be provided on the upper part 406 of the sensor module, the lower part 407 of the sensor module or both the upper and lower parts 406 407 of the sensor module.

Figure 4B:
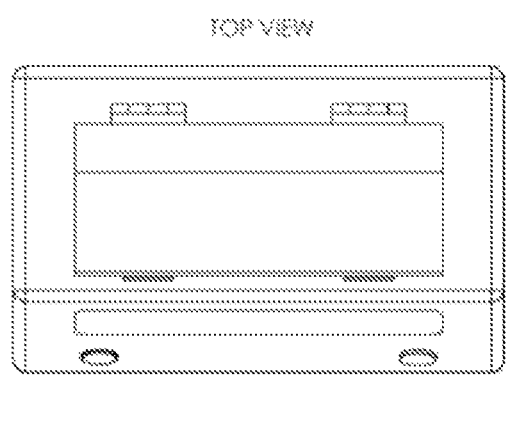
FIG. 4B provides top, side and front views of the device of FIG. 4A.
Figure 4B:
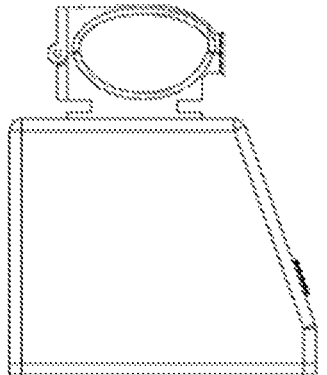
Figure 4B:
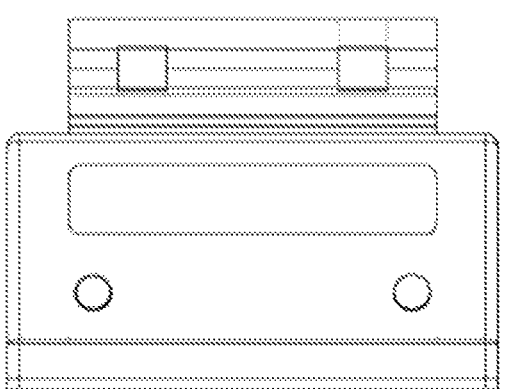

FIG. 4B provides top, side and front views of the device of FIG. 4A.

Figure 5:
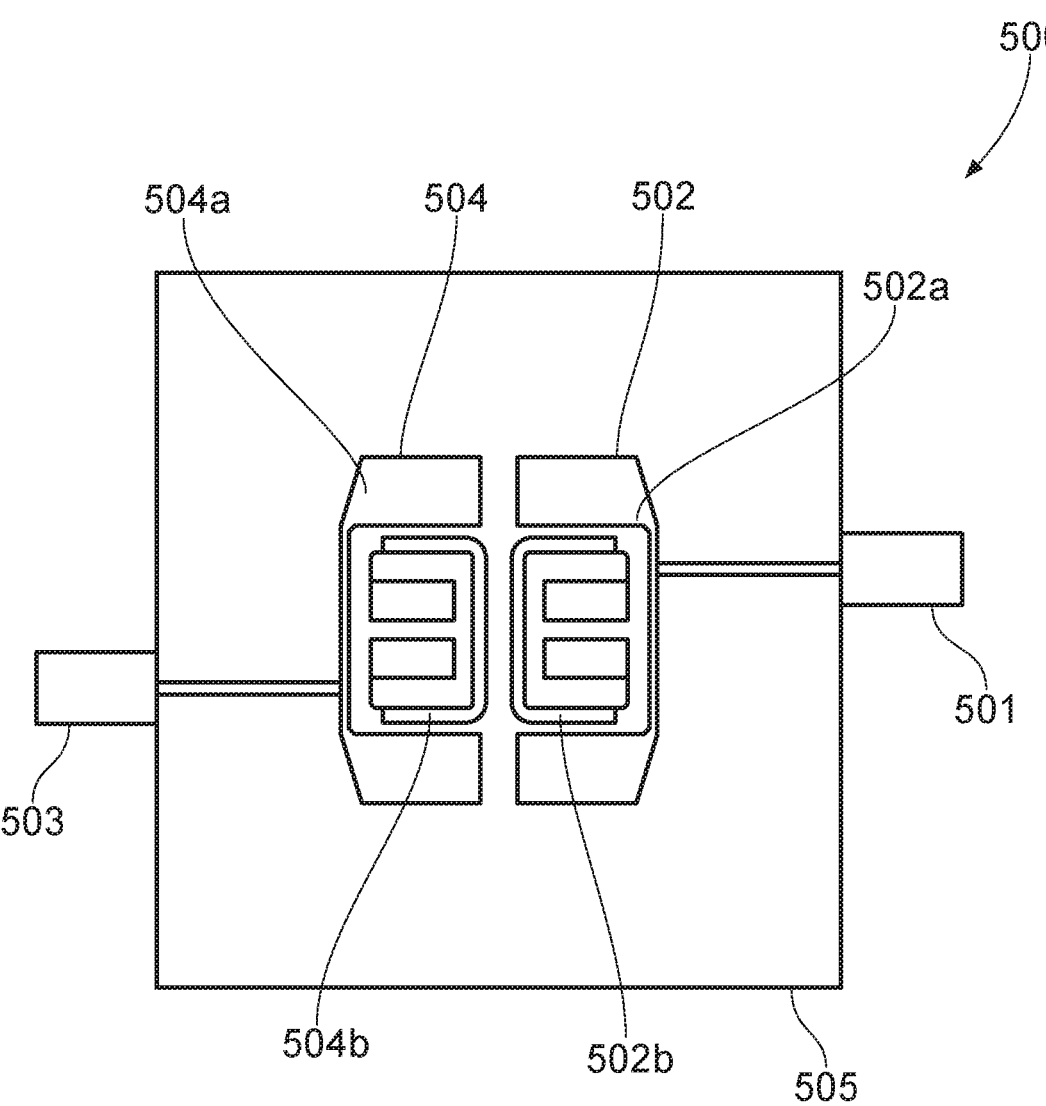
FIG. 5 shows a microwave resonance sensor that can be used in devices in accordance with embodiments of the invention.

FIG. 5 shows a microwave resonance sensor 500 which can be used in devices in accordance with embodiments of the invention.

The sensor 500 is a hairpin sensor.

The sensor 500 includes a first electrical connection port 501 connected to a first pad 502 and a second electrical connection port 503 connected to a second pad 504. The pads 502 504 are disposed on an insulating substrate 505. Each pad 502, 504 comprises a transmission antenna 502a, 504a and a receiving antenna 504a, 504b. This arrangement provides improved resonance response (i.e. sensitivity) of the sensor compared with planar sensors having a single transmission antenna and a single receiving antenna.

In use, the ports 501 503 are connected to signal generation and processing modules via corresponding coaxial wires. Microwave frequency signals are applied to the sensor 500 via the first and second ports 501 503 and the resonance characteristics of the sensor 500 are determined to estimate the dielectric properties of an item to which the sensor 500 is applied.

The sensor 500 is arranged to make contact with the skin of a user's extremity during testing.

Advantageously, compared with other microwave resonance sensor arrangements such as IDE (interdigitated electrode) sensor, the hairpin sensor 500 can provide improved sensing properties. In particular, the electric field from the sensor 500 can project further into a subject's extremity, thereby enabling more reliable substance detection. Additionally, the size of the sensor 500 can be readily increased. Advantageously, this can reduce the need for precise placement of the sensor on a user's extremity.

In certain embodiments, the sensor 500 can have a length of approximately 40 mm, a width of approximately 40 mm and a depth of approximately 1.6 mm. In such embodiments, the electrical field generated by the sensor 500 can project approximately 10 mm into a subject's extremity.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure. Accordingly, the various embodiments disclosed herein are not intended to be limiting, with the true scope being indicated by the following claims.

The invention claimed is:

1. A device for transdermally detecting the concentration of one or more substances in a subject's bloodstream, the device comprising:
   a signal generation module arranged to generate microwave frequency signals at one or more discrete frequencies;
   a sensor module comprising at least one microwave resonance sensor arranged to make contact with a subject's skin, the at least one microwave resonance sensor arranged to transmit microwave frequency signals generated by the signal generation module into the subject's body; and a signal processing module connected to the at least one microwave resonance sensor and arranged to:
   detect a first resonance characteristic and a second resonance characteristic of the at least one microwave resonance sensor, and
   process the first resonance characteristic to determine whether said first resonance characteristic satisfies a first predetermined criteria and process the second resonance characteristic to determine whether said second resonance characteristic satisfies a second predetermined criteria in order to determine the concentration of one or more substances in a subject's bloodstream, wherein the first resonance characteristic is a first amplitude response associated with a microwave frequency signal at a first discrete frequency, and the second resonance characteristic is a second amplitude response associated with a microwave frequency signal at a second discrete frequency,
   wherein the signal processing module is adapted to process the first and second resonance characteristics to determine the concentration of one or more substances in a subject's bloodstream by inputting the first and second resonance characteristics into a neural network that is trained to identify a concentration of a substance in a subject's bloodstream.

2. A device as claimed in claim 1, wherein the signal generation module is arranged to selectively generate microwave frequency signals at the first discrete frequency followed by microwave frequency signals at one or more further discrete frequencies, including the second discrete frequency.

3. A device as claimed in claim 1, wherein the signal processing module is arranged to determine that the first amplitude response at the first discrete frequency corresponds with a stored amplitude response at the first discrete frequency of at least one known composition.

4. A device as claimed in claim 3, wherein the signal processing module is arranged to determine that the second amplitude response at the second discrete frequency corresponds with a stored amplitude response at the second discrete frequency of at least one known composition.

5. A device as claimed in claim 3, wherein each known composition comprises at least a first substance and an anolyte.

6. A device as claimed in claim 5, wherein each known composition comprises a predetermined concentration of said anolyte.

7. A device as claimed in claim 1, wherein the one or more microwave resonance sensor is a planar sensor.

8. A device as claimed in claim 7, wherein the one or more microwave resonance sensor comprises a transmission antenna and a receiving antenna.

9. A device as claimed in claim 8, wherein the transmission antenna and the receiving antenna are arranged on a substrate.

10. A device as claimed in claim 9, wherein the substrate is flexible.

11. A device as claimed in claim 7, wherein the one or more microwave resonance sensor comprises a first transmission antenna arranged adjacent a first receiving antenna, and a second transmission antenna arranged adjacent a second receiving antenna.

12. A device as claimed in claim 11, wherein the first transmission antenna and the first receiving antenna are spaced from the second transmission antenna and the second receiving antenna in a plane parallel to the plane of the sensor.

13. A device as claimed in claim 1, wherein the one or more microwave resonance sensors are resonant hairpin sensors.

14. A device as claimed in claim 1, wherein the signal processing module is adapted to process the first and second resonance characteristics to determine the concentration of one or more substances in a subject's bloodstream by comparing the resonance characteristic with a stored resonance characteristic indicative of a concentration of a substance in a subject's bloodstream.

15. A device as claimed in claim 1, wherein the device is arranged to detect the concentration in a subject's bloodstream of one or more of: alcohol, tetrahydrocannabinol, cocaine, lactate, haemoglobin, sodium chloride, potassium chloride and urea.

16. A device as claimed in claim 1, wherein the signal generation module is arranged to generate at least one discrete microwave frequency signal at a frequency that is not less than 0.01 GHz and not greater than 15 GHz.

* * * * *